(12) United States Patent
Büttner et al.

(10) Patent No.: US 12,217,139 B2
(45) Date of Patent: Feb. 4, 2025

(54) TRANSFORMING A TRAINED ARTIFICIAL INTELLIGENCE MODEL INTO A TRUSTWORTHY ARTIFICIAL INTELLIGENCE MODEL

(71) Applicant: Siemens Aktiengesellschaft, Munich (DE)

(72) Inventors: Florian Büttner, Munich (DE); Christian Tomani, Munich (DE)

(73) Assignee: Siemens Aktiengesellschaft, Munich (DE)

(*) Notice: Subject to any disclaimer, the term of this patent is extended or adjusted under 35 U.S.C. 154(b) by 608 days.

(21) Appl. No.: 17/524,204

(22) Filed: Nov. 11, 2021

(65) Prior Publication Data

US 2022/0067588 A1    Mar. 3, 2022

Related U.S. Application Data

(63) Continuation-in-part of application No. 16/653,415, filed on Oct. 15, 2019, now Pat. No. 11,455,531.

(30) Foreign Application Priority Data

Nov. 17, 2020  (EP) ..................... 20208211

(51) Int. Cl.
*G06N 20/00*  (2019.01)
*G06F 21/62*  (2013.01)

(52) U.S. Cl.
CPC ......... *G06N 20/00* (2019.01); *G06F 21/6218* (2013.01)

(58) Field of Classification Search
CPC .......... G06N 20/00; G06N 3/045; G06N 3/08; G06N 3/084; G06N 20/20; G06N 3/04;
(Continued)

(56) References Cited

U.S. PATENT DOCUMENTS 10,740,606 B2 * 8/2020 Metzler .............. G06V 30/1916
11,055,822 B2    7/2021 Ramanujam et al.
(Continued)

OTHER PUBLICATIONS

"Calibrated Language Model Fine-Tuning for In- and Out-of-Distribution Data"; Lingkai Kong, https://arxiv.org/abs/2010.11506, Oct. 22, 2020 (Year: 2020).*

(Continued)

*Primary Examiner* — Michael S Osinski
(74) *Attorney, Agent, or Firm* — Schmeiser, Olsen & Watts, LLP (57) ABSTRACT

The following relates to a computer-implemented method and system for transforming a trained artificial intelligence model into a trustworthy artificial intelligence model, by providing the trained artificial intelligence model via a user interface of a webservice platform, providing a validation data set, which is based on training data of the trained artificial intelligence model, generating generic samples by a computing component of the webservice platform based on the validation data set, and transforming the trained artificial intelligence model by optimizing a calibration based on the generic samples. The transformation of the AI model is performed by a computing component of the web service platform. The input, i.e. the trained artificial intelligence model as well as a validation data set, is provided to the computing component via a user interface of the web service platform. Such a user interface is implemented by any applicable frontend.

19 Claims, 6 Drawing Sheets

(58) Field of Classification Search
CPC . G06N 3/044; G06F 21/6218; G06F 18/2193;
G06F 18/24; G06F 16/55; G06F 16/5854;
G06F 16/9538; A61B 5/7267; A61B
5/0035; G06V 10/774; G06V 10/776;
G06V 10/82; G06V 10/764
See application file for complete search history.

(56) References Cited

U.S. PATENT DOCUMENTS

| | | | |
|---|---|---|---|
| 11,126,891 | B2 | 9/2021 | Romain, II et al. |
| 2013/0254153 | A1* | 9/2013 | Marcheret ............... G06N 7/00 706/59 |
| 2019/0049231 | A1* | 2/2019 | Choi ...................... G01B 7/004 |
| 2019/0130583 | A1 | 5/2019 | Chen et al. |
| 2019/0147220 | A1 | 5/2019 | McCormac et al. |
| 2019/0188510 | A1 | 6/2019 | Han et al. |
| 2019/0295223 | A1 | 9/2019 | Shen et al. |
| 2019/0369598 | A1 | 12/2019 | Kubo |
| 2020/0005168 | A1 | 1/2020 | Bhargava et al. |
| 2020/0210811 | A1* | 7/2020 | Koo ....................... G06N 5/025 |
| 2020/0265307 | A1 | 8/2020 | Suh |
| 2020/0279008 | A1* | 9/2020 | Jain ....................... G06F 16/954 |
| 2020/0293783 | A1 | 9/2020 | Ramaswamy et al. |
| 2021/0042575 | A1* | 2/2021 | Firner ..................... G06N 3/04 |
| 2021/0067807 | A1 | 3/2021 | Lainema |
| 2021/0105451 | A1 | 4/2021 | Oyman et al. |
| 2021/0158161 | A1 | 5/2021 | Louizos et al. |
| 2021/0232980 | A1* | 7/2021 | Velagapudi ............ G06F 18/217 |
| 2021/0248716 | A1 | 8/2021 | Vera-Gonzalez et al. |
| 2021/0272253 | A1 | 9/2021 | Lin et al. |
| 2021/0279513 | A1 | 9/2021 | Jie |
| 2021/0279577 | A1* | 9/2021 | West ...................... G06N 3/045 |
| 2021/0326576 | A1 | 10/2021 | Liang et al. |
| 2021/0374907 | A1 | 12/2021 | Su |
| 2021/0374913 | A1 | 12/2021 | Su |
| 2021/0407041 | A1 | 12/2021 | Liu et al. |
| 2021/0407086 | A1 | 12/2021 | Liu |
| 2022/0004848 | A1 | 1/2022 | Hoydis et al. |
| 2022/0012898 | A1 | 1/2022 | Carreira et al. |
| 2022/0019855 | A1 | 1/2022 | Chen et al. |
| 2022/0027536 | A1 | 1/2022 | Dutta et al. |
| 2022/0051416 | A1 | 2/2022 | Cao et al. |
| 2022/0067115 | A1 | 3/2022 | Zheng et al. |
| 2022/0067442 | A1 | 3/2022 | Masse et al. |
| 2022/0121902 | A1 | 4/2022 | Hann et al. |
| 2022/0148299 | A1 | 5/2022 | Bonnevie et al. |
| 2022/0268964 | A1* | 8/2022 | Choi ...................... G01W 1/14 |
| 2022/0414464 | A1* | 12/2022 | Krishnaswamy ...... G06N 3/047 |

OTHER PUBLICATIONS

"Ethics guidelines for trustworthy AI" by the European Commission; Apr. 8, 2019;(https://ec.europa.eu/digital-single-market/en/news/ethics-guidelines-trustworthy-ai); Apr. 8, 2019.
Notice of Allowance (Mail Date May 26, 2022) for U.S. Appl. No. 16/653,415, filed Oct. 15, 2019.

* cited by examiner

TRANSFORMING A TRAINED ARTIFICIAL INTELLIGENCE MODEL INTO A TRUSTWORTHY ARTIFICIAL INTELLIGENCE MODEL

CROSS-REFERENCE TO RELATED APPLICATIONS

This application is a continuation-in-part of application Ser. No. 16/653,415, filed Oct. 15, 2019, and claims priority to EP Application No. 20208211.1, having a filing date of Nov. 17, 2020, the entire contents both of which are hereby incorporated by reference.

FIELD OF TECHNOLOGY

The following relates to a computer-implemented method and a system for transforming a trained artificial intelligence model into a trustworthy artificial intelligence model.

BACKGROUND

To facilitate a wide-spread acceptance of artificial intelligence (AI) systems guiding decision making in real-world applications, trustworthiness of deployed models is key. Not only in safety-critical applications such as autonomous driving or Computer-aided Diagnosis Systems (CDS), but also in dynamic open world systems in industry it is crucial for predictive models to be uncertainty-aware and yield well-calibrated—and thus trustworthy—predictions for both in-domain samples ("known unknowns") as well as out-of-domain samples ("unknown unknowns"). In particular, in industrial and IoT settings deployed models may encounter erroneous and inconsistent inputs far away from the input domain throughout the life-cycle. In addition, the distribution of the input data may gradually move away from the distribution of the training data, e.g. due to wear and tear of the assets, maintenance procedures or change in usage patterns etc. The importance of technical robustness and safety in such settings is also highlighted by the recently published "Ethics guidelines for trustworthy AI" by the European Commission (https://ec.europa.eu/digital-single-market/en/news/ethics-guidelines-trustworthy-ai), requiring for trustworthy AI to be lawful, ethical and robust—technically and taking into account its social environment.

In conventional approaches, for each new asset or new environment a new model is trained. However, this is costly, since production has to be stopped during the acquisition of new training data, labeling is expensive and also the procedure of training models comes at a high cost of human and IT resources.

Moreover, statistical methods to detect domain drift based on the input data are known. These methods are highly specific to individual data sets. As known methods are not able to determine the effect of potential data drifts on the accuracy, a retraining of the model as well as a data generation process is necessary.

Common approaches to account for predictive uncertainty include post-processing steps for trained neural networks (NN) and training probabilistic models, including Bayesian and non-Bayesian approaches. However, training such intrinsically uncertainty aware models from scratch comes at a high computational the cost. Moreover, highly specialized knowledge is needed to implement and train such models.

However, while an increasing predictive entropy for an increasingly strong domain drift or perturbations can be an indicator for uncertainty-awareness, simply high predictive entropy is not sufficient for trustworthy predictions. For example, if the entropy is too high, the model will yield under-confident predictions and similarly, if the entropy is too low, predictions will be over-confident.

SUMMARY

Considering the described drawbacks in the state-of-the-art, an aspect relates to provide a method and corresponding computer program product (non-transitory computer readable storage medium having instructions, which when executed by a processor, perform actions) and apparatus for providing a trustworthy artificial intelligence model.

Embodiments of the invention relate to a computer-implemented method for transforming a trained artificial intelligence model into a trustworthy artificial intelligence model, providing the trained artificial intelligence model via a user interface of a webservice platform,
providing a validation data set, which is based on training data of the trained artificial intelligence model,
generating generic samples by a computing component of the webservice platform based on the validation data set,
transforming the trained artificial intelligence model by optimizing a calibration based on the generic samples.

A conventional trained artificial intelligence (AI) model is provided as an input for the proposed method. Any trained AI model might be used and there is no specific requirement on the training level or on a maturity level or on the accuracy of the model. The higher the quality of the trained model, the easier and faster can the method be performed. Moreover the provided trustworthy artificial intelligence model has a corresponding better quality.

As AI-models, for example AI based classifiers are used. For example, machine learning models might be used, e.g. deep learning-based models, neural networks, logistic regression models, random forest models, support vector machine models or tree-based models with decision trees as a basis might be used according to the application the AI-model is to be used for.

Any set of training data, which has been used to train the model or which has been generated or were collected in order to train the model can be used to extract a validation data set. Thereby the validation data set can be the training data or a sub-set or a part of the training data or can be derived from the training data. The validation data set in particular comprises a set of labelled sample pairs, also referred to as samples.

The transformation of the AI model is performed by a computing component of the web service platform. The input, i.e. the trained artificial intelligence model as well as a validation data set, is provided therefor to the computing component via a user interface of the web service platform. Such a user interface can be implemented by any applicable frontend, for example by a web app.

The validation data set can be provided via the same user interface of the web service platform. Moreover, the training data set can be provided by the user interface and a validation data set is derived from the training data by the computing component.

Based on the validation data set, generic samples are generated. Those generic samples reflect a domain drift, whereby, in an embodiment, a plurality of generic samples is generated, reflecting different levels or different degrees of domain drift. In other words, a plurality of generic samples is generated representing different strengths of perturbations. Those perturbations can reflect predictable or foreseeable or likely influences on the expected in-domain samples or they can alternatively reflect purely random modifications of the samples or they might further alternative reflect specific intended modifications in the sense of generation of adversarial samples. Thereby, a spectrum ranging from in-domain samples to out-of-domain samples is generated in an embodiment. Samples in more detail are sample pairs. A pair comprises an input object, in particular a vector or matrix, and a desired output value or label, also called the supervisory signal. According to this, the model input can be equally referred to as input object and the model output can be equally referred to as output value or label. The input of a sample from the validation data set is adapted to reflect the domain drift.

Based on the generated generic examples, the calibration is optimized. This can be achieved e.g. within a step of adapting the AI model, especially weights of a neural network, or within the step of postprocessing outputs of an AI model.

Optimizing the calibration based on the generic samples results in an AI model that ensures interpretability for the predicted probabilities for the different classes of a classifier. Optimizing the calibration is in contrast to conventional approaches, where the accuracy is optimized. Moreover, in contrast to conventional approaches, not only adversarial samples in terms of attacks are used, but samples underlying a domain drift, in particular a domain drift with varying perturbation level. Combining the generation of generic samples with an optimization of the calibration based on those generic samples is the differentiator over conventional approaches and leads to the advantages described herein.

The calibration is optimized, so that so-called confidence scores, meaning probabilities for a specific class, match an accuracy. Therefore, a confidence derived from the trustworthy AI model corresponds to a certain degree of certainty.

As the calibration is performed with the help of the generated generic samples, the confidence matches the accuracy for all levels of perturbations which are reflected in the generic samples.

The step of optimizing the calibration therefore links confidence-scores or probabilities with accuracy over the whole range of generic samples. The calibrated trustworthy AI model predicts well-calibrated uncertainties, with the confidence, e.g. the entropy, matching the actual predictive power of the model.

The method enables the transformation of an AI model into a trustworthy AI model by using an uncertainty aware calibration optimization method. The trustworthy AI model determines trustworthy probabilities for both in-domain samples as well as out-of-domain samples.

The trustworthy AI model in embodiments is an adapted model based on the AI model and e.g. adapted in terms of weights of knots within a neural network or in other embodiments is an extended AI model comprising a post-processing algorithm.

In an advantageous manner, overconfident predictions are avoided using the trustworthy AI model obtained with the proposed method. Using the trustworthy AI model, a user knows that when a confidence decreases also the accuracy decreases in a coordinated fashion, so that the user can make an informed decision on when to re-train or replace an AI model. Moreover, in instant feedback on the prediction quality is received by analyzing the accuracy of the trustworthy AI model for given inputs in a real-world scenario. In an advantageous manner, the user instantly knows, whether an AI model can be used for example in a new context, for example a new factory, or whether it needs to be re-trained, potentially saving substantially efforts for unnecessary data collection and model training.

A method is proposed to automatically transform conventional neural networks. For the proposed method, there is no expert scientist necessary to provide custom implementations of modified neural networks. Lay users are enabled to integrate trustworthiness in any machine learning development pipeline. Trustworthy AI is therefore made accessible to a large user base of applied practitioners without expert knowledge.

With the transformation method which optimizes the calibration, the architecture or structure of the AI model is not affected, so that the trustworthy AI model can be deployed directly for the intended use case or application without a further mandatory validation phase. This is the case in particular for transformation methods based on a re-training of the AI model or a postprocessing of the output of the AI model. These characteristics of the method enable the usage as a webservice, so that starting from a pre-trained AI-model, the transformation is offered as a service by a cloud platform in particular.

According to an embodiment, by optimizing the calibration, an uncertainty-awareness is represented in a confidence-level for any of the generic samples. In case, that the AI model realizes a certain level of uncertainty, a predicted classification is equally distributed among the given classes of the classifier. This for example leads to a low and equally distributed confidence score. This is achieved for example by assigning a high entropy in case of an uncertain classification result, and for example via adapting the objective function of the AI model or postprocessing outputs of the AI model.

Depending on the concrete method used for transforming the trained AI model, a re-training of the AI model or a post-processing of outputs of AI model or any further suitable transforming methods are performed. For retraining methods, in an embodiment only a small validation data set is necessary if the trained AI model is a substantially mature trained AI model. In case of only roughly pre-trained AI models, a retraining based on a more comprehensive validation data set is performed in an embodiment. For post-processing methods, there is no influence on the AI model in terms of structure or architecture, in particular no weights are adapted, so that the trained AI model is provided on a refined level in an embodiment, so that the calibrated trustworthy AI model can be applied after the transformation directly.

According to an embodiment, for generating the generic samples the validation data set is modified by a domain-drift. More specifically, the validation data set is modified by an algorithm representing a domain drift. For example, samples of the validation data set can be modified by adding noise signal. In an embodiment, the validation data set is modified in a way, that typical drift an industrial environment is represented, for example due to contaminated camera lenses, vibrations, etc.

According to an embodiment, for generating the generic samples the validation data set is modified according to perturbation strengths. With this modification, different levels of perturbations are achieved. In an embodiment, generic samples are generated that reflect perturbations ranging from typical domain drift within an industrial environment to modifications that reflect truly out of domain samples.

According to an embodiment, transforming comprises applying an entropy-based loss term which encourages uncertainty-awareness. Such an entropy-based loss term is used for a neural network based AI model in an embodiment. In an embodiment, an entropy loss term is provided in addition to a convenient loss term, e.g. a cross entropy loss term. With these combined loss terms, the neural network is encouraged towards a uniformly distributed softmax output in case of uncertainty.

According to an embodiment, transforming further comprises performing a re-training of the AI-model with applying a calibration loss term. By combining an entropy-based loss term with a calibration loss term, the technical robustness of the model is increased for inputs that are close or similar to the validation data or training data.

According to an embodiment, the following steps are performed:
 computing a categorical cross-entropy loss for the validation data set based on current outputs of the trained AI model and corresponding ground truth data of the validation data set;
 computing a predictive entropy loss by removing non-misleading evidence from the current outputs and distributing the remaining current outputs over a predetermined number of classes;
 computing a combined loss by adding to the categorical cross-entropy loss the predictive entropy loss weighted with a predetermined first loss factor $\lambda_S$, where $0 <= \lambda_S <= 1$;
 checking whether the re-training converged to a predefined lower limit for a convergence rate;
 updating weights of the AI model based on the combined loss and a predetermined training rate $\eta$, where $0 < \eta <= 1$, in case the re-training did not converge; and
 stopping the re-training of the AI model in case the re-training converged.

Encouraging a high entropy with the proposed combined loss term encourages the model towards a uniformly distributed probability distribution, for example the output of the softmax function, in case of uncertainty.

According to an embodiment, further the following steps are performed:
 generating perturbed outputs of the for the generic samples by forward propagating the generic input data of the generic samples in the AI model;
 computing a calibration loss as the Euclidian norm of an expected calibration error, which takes a weighted average over the perturbed outputs grouped in a predefined number of equally spaced bins each having an associated average confidence and accuracy;
 checking whether the re-training converged to a predefined lower limit for a convergence rate;
 first time updating weights of the AI model based on the combined loss and a predetermined training rate $\eta$, where $0 < \eta <= 1$, in case the training did not converge;
 second time updating the weights of the AI model based on the calibration loss weighted with a predetermined second loss factor $\lambda_{adv}$, where $0 <= \lambda_{adv} <= 1$, and the predetermined training rate in case the training did not converge; and
 stopping the training of the in case the training converged.

With the proposed calibration loss term, the technical robustness of the AI model increases for inputs built of the validation data set or training samples of the validation data set and underlying a variety of perturbation levels.

According to an embodiment, the artificial intelligence model is a neural network.

An embodiment with combined loss term and calibration loss term is described in more detail. A computer-implemented method of re-training a neural network in order to transform a trained neural network into a trustworthy neural network comprises the steps of receiving a validation data set T of validation input data $X=(X_1, \ldots, X_n)$ and corresponding ground truth data $Y=(Y_1, \ldots, Y_n)$ for a predetermined number C of classes. Thereby, n is greater than one (n>1) and C is greater than or equal to one (C>=1). The step of re-training the neural network comprises the iterative training steps selecting a validation sub-set, generating current outputs, computing a categorical cross-entropy loss, computing a predictive entropy loss, computing a combined loss, providing a perturbation level, generating a generic sample set, generating perturbed outputs, computing a calibration loss, checking whether the training converged, first time updating weights, second time updating the weights and stopping the training. In the training step of selecting a validation sub-set, a validation sub-set B of validation input data $X_B$ and corresponding ground truth data $Y_B$ is selected from the validation set T. Thereby, the cardinal number of the validation sub-set is greater than zero and smaller than the cardinal number of the validation set ($0<|\beta|<|T|$).

In the re-training step of generating current outputs, current outputs of the neural network for the sub-set B are generated by forward propagating the validation input data $X_B$ of the training sub-set B in the neural network. In the re-training step of computing a categorical cross-entropy loss, a categorical cross-entropy loss $L_{CCE}$ for the sub-set B is computed based on the current outputs and the corresponding ground truth data $Y_B$ of the training sub-set B. In the re-training step of computing a predictive entropy loss, a predictive entropy loss $L_S$ is computed by removing non-misleading evidence from the current outputs and distributing the remaining current outputs over the predetermined number C of classes. In the re-training step of computing a combined loss, a combined loss L is computed by adding to the categorical cross-entropy loss $L_{CCE}$ the predictive entropy loss $L_S$ weighted with a predetermined first loss factor $\lambda_S$. Thereby, the first loss factor $\lambda_S$ is greater than or equal to zero and smaller than or equal to 1 ($0<=\lambda_S<=1$).

In the re-training step of providing or sampling a perturbation level, a perturbation level $\varepsilon_B$ is randomly sampled with a value from 0 to 1. In the re-training step of generating an generic sample set, a generic sample set $B_g$ of generic input data $X_g$ is generated by applying a perturbation randomly selected from a predefined set of perturbations and weighted with the perturbation level $\varepsilon_B$ to the validation input data $X_B$ of the validation sub-set B. Thereby the cardinal number of the generic input data is equal to the cardinal number of the validation input data of the validation sub-set ($|X_{adv}|=|X_B|$). In the re-training step of generating perturbed outputs, perturbed outputs of the neural network for the generic sample set $B_g$ are generated by forward propagating the generic input data $X_g$ of the generic sample set $B_g$ in the neural network in the training step of computing a calibration loss, a calibration $loss_{Lg}$ is computed as the Euclidian norm ($L_2$ norm) of an expected calibration error ECE. The expected calibration error ECE takes a weighted average over the perturbed outputs grouped in a predefined number M of equally spaced bins each having an associated average confidence and accuracy. Thereby the predefined number M is greater than one (M>1).

In the re-training step of checking whether the training converged, it is checked whether the training converged to a predefined lower limit for a convergence rate. In the step of first time updating weights, weights of the neural network are updated first time based on based on the combined loss L and a predetermined training rate η, where the predetermined training rate η is greater than zero and smaller than or equal to one ($0<\eta<=1$), in case the training did not converge.

In the step of second time updating weights, weights of the neural network are updated second time based on the calibration loss $L_g$ weighted with a predetermined second loss factor $\lambda_g$, where the predetermined second loss factor $\lambda_g$ is greater than or equal to zero and smaller than or equal to one ($0<=\lambda_{adv}<=1$), and the predetermined training rate η, in case the training did not converge. In the step of stopping the training, the training of the neural network is stopped in case the training converged.

The received validation data set T also comprises the corresponding ground truth data Y. The ground truth data Y comprises multiple samples of ground truth data $Y_1$ to $Y_n$ that corresponds to the respective samples of the validation input data $X_1$ to $X_n$. The corresponding ground truth data gives the information that is to be deduced by the neural network.

Each pair of sample of validation input data and corresponding sample of ground truth data $X_1$, $Y_1$ to $X_n$, $Y_n$ belongs to one of the classes.

For example, the samples of validation input data $X_1$ to $X_n$ may be different images showing handwritten numbers and the corresponding samples of ground truth data $Y_1$ to $Y_n$ may be the respective number that is to be deduced by the neural network. The classes may be C=10 classes where each class represents one number (0 to 9). Here the C=10 classes could be one-hot encoded in the following way:

0 corresponds to 1 0 0 0 0 0 0 0 0 0
1 corresponds to 0 1 0 0 0 0 0 0 0 0
2 corresponds to 0 0 1 0 0 0 0 0 0 0
3 corresponds to 0 0 0 1 0 0 0 0 0 0
4 corresponds to 0 0 0 0 1 0 0 0 0 0
5 corresponds to 0 0 0 0 0 1 0 0 0 0
6 corresponds to 0 0 0 0 0 0 1 0 0 0
7 corresponds to 0 0 0 0 0 0 0 1 0 0
8 corresponds to 0 0 0 0 0 0 0 0 1 0
9 corresponds to 0 0 0 0 0 0 0 0 0 1

As another example, the samples of validation input data $X_1$ to $X_n$ may be different medical image data like Magnetic Resonance images, Computer Tomography images, Sonography images etc. and the corresponding samples of ground truth data $Y_1$ to $Y_n$ may be respective maps where each pixel or voxel of the medical image data is assigned a different type of tissue or organ that is to be deduced by the NN. The classes may be C=3 classes where each class represents one type of tissue. Here the C=3 classes could be one-hot encoded in the following way:

normal tissue corresponds to 1 0 0
tumorous tissue corresponds to 0 1 0
fibrous tissue corresponds to 0 0 1

Alternatively, the classes may be C=4 classes where each class represents one type of organ. Here the C=4 classes could be one-hot encoded in the following way:

lung tissue corresponds to 1 0 0 0
heart tissue corresponds to 0 1 0 0
bone corresponds to 0 0 1 0
other tissue corresponds to 0 0 0 1

As another example, the samples of validation input data $X_1$ to $X_n$ may be data of varying courses of different physical quantities like force, temperature, speed etc. and the corresponding samples of ground truth data $Y_1$ to $Y_n$ may be respective state of a machine that is to be deduced by the neural network. The classes may be C=3 classes where each class represents one state of the machine. Here the C=3 classes could be one-hot encoded in the following way:

normal operation corresponds to 1 0 0
start-up phase corresponds to 0 1 0
failure corresponds to 0 0 1

As another example, the samples of validation input data $X_1$ to $X_n$ may be texts regarding different topics like politics, sports, economics, science etc. and the corresponding samples of ground truth data $Y_1$ to $Y_n$ may be the respective topic that is to be deduced by the neural network. The classes may be C=4 classes where each class represents one topic. Here the C=4 classes could be one-hot encoded in the following way:

politics corresponds to 1 0 0 0
sports corresponds to 0 1 0 0
economics corresponds to 0 0 1 0
sciences corresponds to 0 0 0 1

According to an embodiment, transforming comprises post-processing an output of the AI model. In an embodiment, when performing a post-processing, the AI model does not have to be retrained in order to be transformed into the trustworthy AI model. Therefore, the AI model does not have to be provided detailed architectural information. That means that even black box classifiers can be transformed with the proposed method. The step of post-processing itself can be interpreted as a step of learning a post-processing-model and is not to be mixed with the training of the AI model provided by the user of the webservice platform.

The post-processing can be parametric or non-parametric. An example of a parametric post-processing method is Platt's method that applies a sigmoidal transformation that maps the output of a predictive model to a calibrated probability output. The parameters of the sigmoidal transformation function are learned using a maximum likelihood estimation framework. The most common non-parametric methods are based either on binning (Zadrozny and Elkan 2001) or isotonic regression (Zadrozny and Elkan 2002). For example, histogram binning is used introduced by Naeini, M. P., Cooper, G. F., & Hauskrecht, M. (2015, January) for obtaining well calibrated probabilities using bayesian binning.

For the post-processing, again generic samples are generated and fed into the trained AI model. The output of the trained AI model impinged with the generic samples is then calibrated.

In an embodiment, a set of samples covering the entire spectrum from in-domain samples to truly out-of-domain samples in a continuous and representative manner is generated. For example, the fast gradient sign method is applied to the validation data set to generate generic samples, with varying perturbation strength. More specifically, for each sample in the validation set, the derivative of the loss with respect to each input dimension is computed and the sign of this gradient is recorded. If the gradient cannot be computed analytically, e.g. for decision trees, a 0th-order approximation is performed, computing the gradient using finite differences. Then noise c is added to each input dimension in the direction of its gradient.

In an embodiment, for each sample, a noise level is picked at random, such that the generic validation set comprises representative samples from the entire spectrum of domain drift. For image data affine image transformations are applied, e.g. rotation, translation, etc., and image corruptions, like blur, speckle noise, etc.

According to an embodiment, during the step of post-processing, parameters of a monotonic function used to transform unnormalized logits are determined by optimizing a calibration metric based on the generic samples. For example, a strictly monotonic function, in particular a piecewise temperature scaling function or a platt scaling function or other related parameterizations of a monotonic function, is used to transform unnormalized logits of a classifier into post-processed logits of the classifier. The parameters of the function, e.g. the temperatures, are then determined by optimizing a calibration metric based on the generic samples. Such calibration metrics are for example the log likelihood, the Brier score, Nelder Mead or the expected calibration error. Performing e.g. the temperature scaling, i.e. learning the temperature, based on the generic samples and not based on the validation data set (or training data set) results in a well-calibrated AI model, extended in order to comprise a post-processing step, under domain shift.

Another advantage is that the method has no negative effect on the accuracy. The method ensures that the classifier is well calibrated not only for in-domain predictions but yields well calibrated predictions also under domain drift.

Method according to, wherein the artificial intelligence model is a classifier, in particular one of deep neural network, gradient boosted decision tree, xgboost, support vector machine, random forest and neural network.

According to an embodiment, the validation data set is a sub-set of the training data of the trained artificial intelligence model. In an embodiment, a user only has to provide this sub-set of the training data and does not have to provide an entire training data set.

According to an embodiment, the validation data set is generated by modifying the training data of the trained artificial intelligence model. The method step of modifying the training data to generate the validation data that can be part of method steps performed by the computing unit of the web service platform or can be performed in advance, so that a user only provides the validation data set via the user interface.

According to an embodiment, the transformed artificial intelligence model is provided via the user interface of the webservice platform, in particular as downloadable file. In an advantageous manner, the user inputs a not necessarily trustworthy AI model and receives a transformed trustworthy AI model.

Embodiments of the invention moreover relate to a computer program product comprising instructions which, when executed by a computing component, cause the computing component to carry out the method. The computing component for example is a processor and for example is connectable to a human machine interface. The computer program product may be embodied as a function, as a routine, as a program code or as an executable object, in particular stored on a storage device.

Embodiments of the invention moreover relates to a system for transforming a trained artificial intelligence model into a trustworthy artificial intelligence model, comprising:
  a user interface component to enable provision of the trained artificial intelligence model,
  a memory storing the trained artificial intelligence model and user assignment information,
  a computing component for generating generic samples based on a validation data set, wherein the validation data set is determined based on training data of the trained artificial intelligence model, and for transforming the trained artificial intelligence model by optimizing a calibration based on the generic samples.

For example, the computing component may comprise a central processing unit (CPU) and a memory operatively connected to the CPU.

In an embodiment, the system enables lay users to transform their pre-trained AI model into a trustworthy AI model within a detachable step, including the option to use the system anytime, for example flexibly after a retraining phase of the trust with the calibrated AI model, which has for example be necessary due to changed applications or scenarios the AI model is used for.

According to an embodiment, the user interface of the system is accessible via a web service. This enables the user to flexibly provide the AI model and corresponding training data or validation data. The user has a transparent overview of the extent to which data and information about the AI model and corresponding data is provided.

According to an embodiment, the memory and the computing component are implemented on a cloud platform. This enables a flexible adaption to the extent the web service is requested, in particular in terms of computing power.

Moreover, customer specific requirements in terms of server locations can be flexibly handled with the usage of a cloud computing platform.

Further possible implementations or alternative solutions of embodiments of the invention also encompass combinations—that are not explicitly mentioned herein—of features described above or below with regard to the embodiments. The person skilled in the art may also add individual or isolated aspects and features to the most basic form of embodiments of the invention.

BRIEF DESCRIPTION

Some of the embodiments will be described in detail, with reference to the following figures, wherein like designations denote like members, wherein.

DETAILED DESCRIPTION

Figure 1:
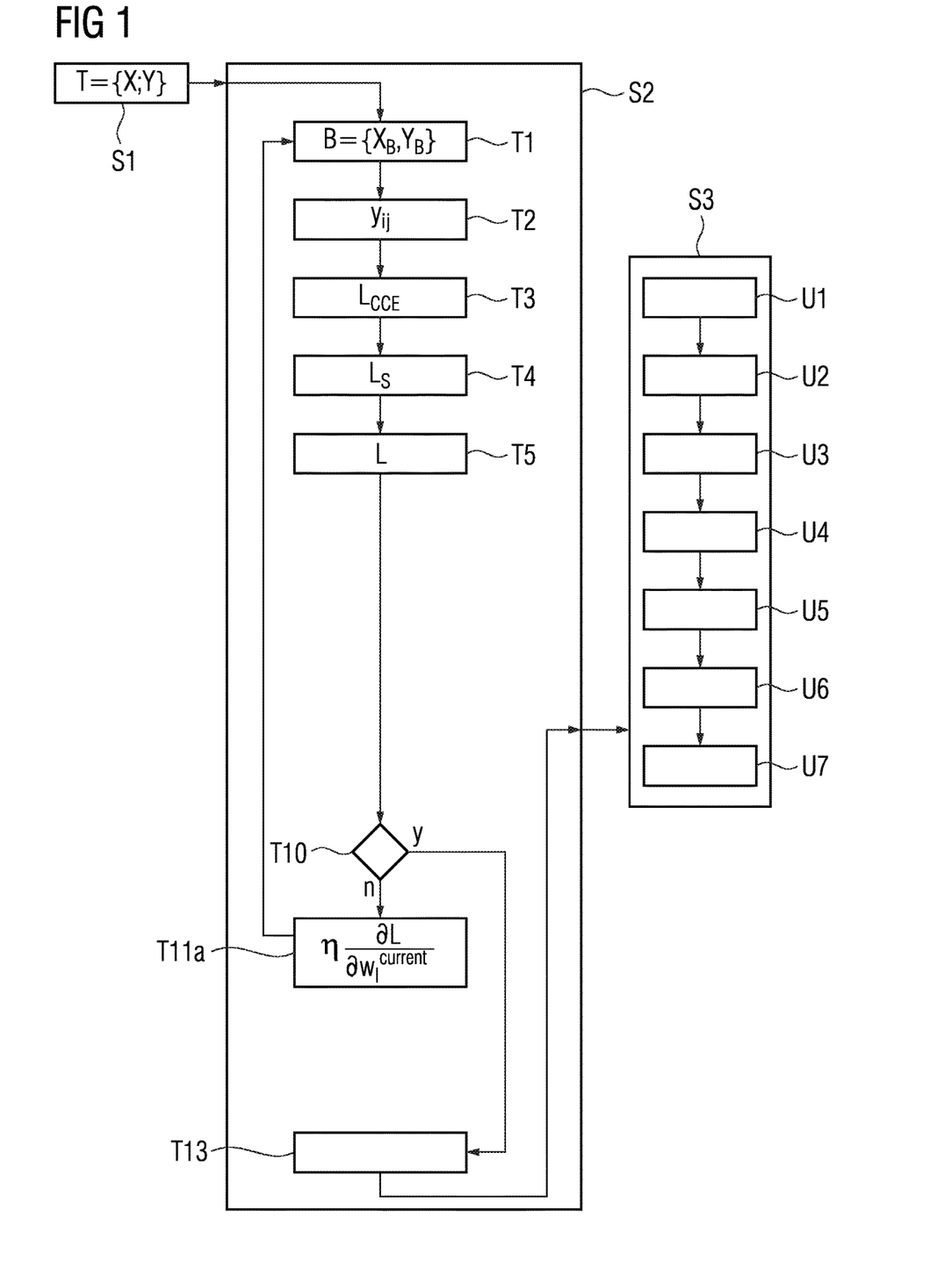
FIG. 1 shows a schematic flow chart of the method of training a NN according to a first aspect.

In FIG. 1 the method of training a NN according to the first aspect is schematically depicted. The method comprises the steps receiving S1 a training set, training S2 the NN and optionally evaluating S3 a robustness of the trained NN.

In the step of receiving S1 a training set, exemplarily a training set $T=\{X; Y\}$ of training input data $X=(X_1, \ldots, X_{1000})$ that are hand written images of numbers from 0 to 9 and corresponding ground truth data $Y=(Y_1, \ldots, Y_{1000})$ that are the corresponding numbers for the ten classes (C=10) that resemble the possible numbers from 0 to 9 is received.

Here the C=10 classes are one-hot encoded in the following way:
  0 corresponds to 1 0 0 0 0 0 0 0 0 0
  1 corresponds to 0 1 0 0 0 0 0 0 0 0
  2 corresponds to 0 0 1 0 0 0 0 0 0 0
  3 corresponds to 0 0 0 1 0 0 0 0 0 0
  4 corresponds to 0 0 0 0 1 0 0 0 0 0
  5 corresponds to 0 0 0 0 0 1 0 0 0 0
  6 corresponds to 0 0 0 0 0 0 1 0 0 0
  7 corresponds to 0 0 0 0 0 0 0 1 0 0
  8 corresponds to 0 0 0 0 0 0 0 0 1 0
  9 corresponds to 0 0 0 0 0 0 0 0 0 1

The step of training S2 the NN comprises the iterative training steps selecting T1 a training sub-set, generating T2 current outputs, computing T3 a categorical cross-entropy loss, computing T4 a predictive entropy loss, computing T5 a combined loss, checking T10 whether the training converged, updating T11a weights and stopping T13 the training.

In the training step of selecting T1 a training sub-set, exemplarily a training sub-set B={$X_B$; $Y_B$} of training input data $X_B=(X_{B,1}, \ldots, X_{B,100})$ that are 100 randomly selected images from the training set T and corresponding ground truth data $Y_B=(Y_{B,1}, \ldots, Y_{B,100})$ that are the corresponding numbers is randomly selected from the training set T.

In the training step of generating T2 current outputs, current outputs $y_{ij}$ of the NN for the sub-set B are generated by forward propagating the exemplarily 100 images of the training input data $X_B$ of the training sub-set B in the NN.

In the training step of computing T3 a categorical cross-entropy loss, a categorical cross-entropy loss $L_{CCE}$ for the sub-set B is computed based on the current outputs $y_{ij}$ and the corresponding ground truth data $Y_B$ of the training sub-set B.

In the training step of computing T4 a predictive entropy loss, a predictive entropy loss $L_S$ is computed. Thereto, non-misleading evidence (probability of one class is set to one and all other probabilities of the remaining classes are set to zero) is removed from the current outputs $y_{ij}$. The remaining current outputs $y_{ij}$ are then distributed over the ten classes in order to calculate the predictive entropy loss $L_S$. The predictive entropy loss $L_S$ is calculated by the following formula:

$$L_S = \sum_{i=1}^{n}\sum_{j=1}^{C} -\frac{1}{c}\log(p_{ij}(1-y_{ij})+y_{ij})$$

where $p_{ij}$ is the confidence associated with to the jth class of sample i and $y_{ij}$ is its one-hot encoded label.

In the training step of computing T5 a combined loss, a combined loss L is computed by adding to the categorical cross-entropy loss $L_{CCE}$ the predictive entropy loss $L_S$ weighted with a predetermined first loss factor $\lambda_S$ of exemplarily 0.5.

The combined loss L may be calculated by the following formula:

$$L=L_{CCE}+\lambda_S L_S$$

In the training step of checking T10 whether the training converged, it is checked whether the training converged to a predefined lower limit for a convergence rate.

In the step of updating T11a weights, weights $w_l$ of the NN are updated based on the combined loss L and a predetermined training rate η of exemplarily 0.2 in case the training did not converge. Thereto, the combined loss L is back-propagated to the weights $w_l$ of the NN by changing the weights according to the combined loss L. It is determined how much each weight $w_l$ contributes to the combined loss L and then each weight $w_l$ is changed proportionally to its contribution to the combined loss L. Each weight $w_l$ of the NN may be adjusted in the respective step of updating weights by the following formula:

$$w_l^{updated} = w_l^{current} - \eta\frac{\partial L}{\partial w_l^{current}}$$

where $w_l^{current}$ is the current value of the lth weight of the NN, $w_l^{updated}$ is the updated or adjusted value of the lth weight of the NN and $$\frac{\partial L}{\partial w_l^{current}}$$

is the partial derivative of the combined loss L with respect to the lth weight of the NN.

In the step of stopping T13 the training, the training of the NN is stopped in case the training converged.

After the training has converged and the iteration of the step of training S2 the NN is aborted, the NN is completely trained. Optionally, the trained NN can be evaluated in the optional step of evaluating S3 a robustness of the trained NN that comprises the sub-steps providing U1 the trained NN with a first set, generating U2 perturbed outputs, computing U3 the ECEs for the respective generated outputs, providing U4 the trained NN with at least one further set of multiple perturbed input datasets, generating U5 perturbed outputs of the NN based on the provided at least one further set of multiple perturbed input datasets, computing U6 the ECEs for the respective generated outputs and calculating U7 micro-averaged ECEs.

In the sub-step of providing U1 the trained NN with a first set, the NN is provided with a first set of multiple perturbed input datasets. The multiple perturbed input datasets have been perturbed with a perturbation of a first perturbation-type. Thereby, each input dataset has been perturbed with a different predefined perturbation level $\varepsilon_B$.

In the sub-step of generating U2 perturbed outputs of the NN, perturbed outputs of the NN are generated based on the provided first set multiple perturbed input datasets.

In the sub-step of computing U3 the ECEs for the respective generated outputs, the ECEs are computed for the respective generated outputs. The expected calibration errors ECEs are calculated for the respective generated outputs in the same way as described above for the outputs during the step of training S2 the NN.

In the sub-step of providing U4 the trained NN with at least one further set of multiple perturbed input datasets, the trained NN is provided with at least one further set of multiple perturbed input datasets. The multiple perturbed input datasets have been perturbed with a perturbation of at least one further perturbation-type. Thereby, each input dataset has been perturbed with a different predefined perturbation level $\varepsilon_B$.

In the sub-step of generating U5 perturbed outputs of the NN based on the provided at least one further set of multiple perturbed input datasets, perturbed outputs of the NN are generated based on the provided at least one further set of multiple perturbed input datasets.

In the sub-step of computing U6 the ECEs for the respective generated outputs, the ECEs are computed for the respective generated outputs. The expected calibration errors ECEs are calculated for the respective generated outputs in the same way as described above for the outputs during the step of training S2 the NN.

In the sub-step of calculating U7 micro-averaged ECEs, micro-averaged ECEs are calculated across the generated outputs of each provided set of multiple perturbed input datasets by calculating the average of the respective ECEs. The micro-averaged ECEs enable a detailed assessment of the trustworthiness or rather robustness of the predictions of the trained NN.

Figure 2:
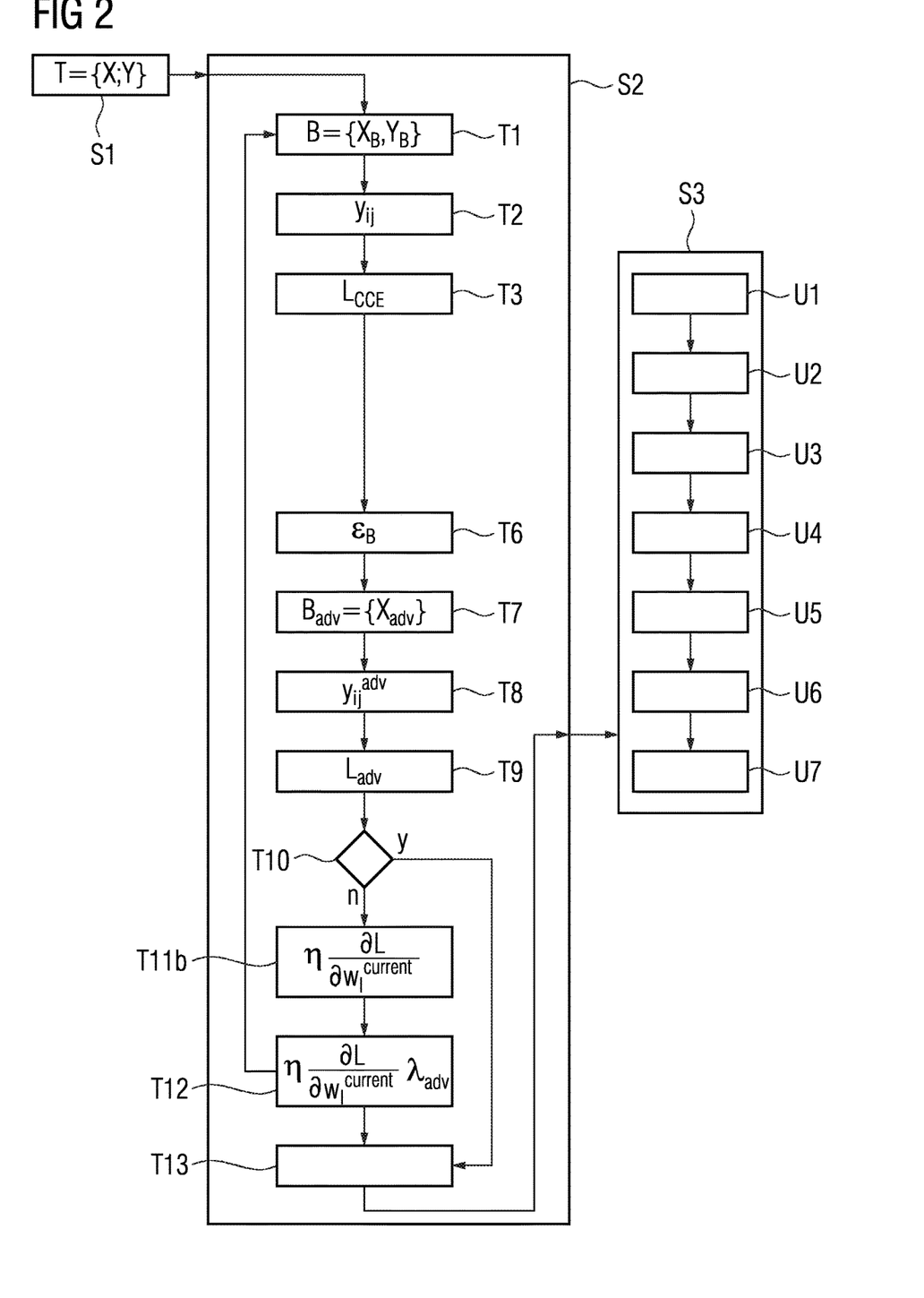
FIG. 2 shows a schematic flow chart of the method of training a NN according to a second aspect.

In FIG. 2 the method of training a NN according to the second aspect is schematically depicted. The method according to the second aspect and as depicted in FIG. 2 is similar to the method according to the first aspect and as depicted in FIG. 1. Therefore, only differences between the two will be described in the following. The step of training S2 the NN of the method of FIG. 2 comprises the training steps sampling T6 a perturbation level, generating T7 an adversarial set, generating T8 perturbed outputs, computing T9 an adversarial calibration loss first time updating T11b weights and second time updating T12 the weights instead of the steps computing T4 a predictive entropy loss, computing T5 a combined loss and updating T11a weights of the step of training S2 the NN of the method of FIG. 1.

In the training step of sampling T6 a perturbation level, a perturbation level $\varepsilon_B$ is randomly sampled from the exemplary set $\varepsilon$ that includes the values 0, 0.05, 0.1, 0.15, 0.2, 0.25, 0.3, 0.35, 0.4, 0.45.

In the training step of generating T7 an adversarial set, an adversarial set $B_{adv}$ of adversarial input data $X_{adv}$ is generated. Thereto, a perturbation is randomly selected from a predefined set of perturbations that exemplarily includes the image-based perturbation types left rotation, right rotation, shift in x direction, shift in y direction, xy shift, shear, zoom in x direction, zoom in y direction and xy zoom. Then the selected perturbation is weighted with the sampled perturbation level $\varepsilon_B$ and applied to the training input data $X_B$ of the training sub-set B. Thereby, the training input data that is to be perturbed (i.e. respective images of a number) is transformed into the adversarial input data $X_{adv}$ (perturbed handwritten images of a number) of the adversarial set $B_{adv}$.

In the training step of generating T8 perturbed outputs, perturbed outputs of the NN for the adversarial set $B_{adv}$ are generated by forward propagating the exemplarily 100 perturbed images as the adversarial input data $X_{adv}$ of the adversarial set $B_{adv}$ in the NN.

In the training step of computing T9 an adversarial calibration loss, an adversarial calibration loss $L_{adv}$ is computed as the Euclidian norm ($L_2$ norm) of an expected calibration error ECE. Thereto, the perturbed outputs are grouped into exemplarily M=10 bins, where each bin covers a confidence interval $I_m$ of size 0.1:
first bin confidence interval $I_m$ between 0 and 0.1
second bin confidence interval $I_m$ between 0.1 and 0.2
third bin confidence interval $I_m$ between 0.2 and 0.3
fourth bin confidence interval $I_m$ between 0.3 and 0.4
fifth bin confidence interval $I_m$ between 0.4 and 0.5
sixth bin confidence interval $I_m$ between 0.5 and 0.6
seventh bin confidence interval $I_m$ between 0.6 and 0.7
eighth bin confidence interval $I_m$ between 0.7 and 0.8
ninth bin confidence interval $I_m$ between 0.8 and 0.9
tenth bin confidence interval $I_m$ between 0.9 and 1

The expected calibration error ECE is calculated by the following formula:

$$ECE = \sum_{m=1}^{M} \frac{|B_m|}{n} |acc(B_m) - conf(B_m)|$$

where $B_m$ is a set of indices of samples whose prediction confidence falls into the associated confidence interval $I_m$, $conf(B_m)$ is the average confidence associated to $B_m$ and $acc(B_m)$ is the accuracy associated to $B_m$.

The adversarial calibration loss $L_{adv}$ is calculated by the following formula:

$$L_{adv} = \|ECE\|_2 = \left\| \sum_{m=1}^{M} \frac{|B_m|}{n} |acc(B_m) - conf(B_m)| \right\|_2$$

In the step of first time updating T11b weights, weights $w_l$ of the NN are updated first time based on the categorical cross-entropy loss $L_{CCE}$ and the predetermined training rate $\eta$ in case the training did not converge.

In the step of second time updating T12 weights, weights of the NN are updated second time based on the adversarial calibration loss $L_{adv}$ weighted with a predetermined second loss factor $\lambda_{adv}$ of exemplarily 0.5 and the predetermined training rate $\eta$, in case the training did not converge.

Figure 3:
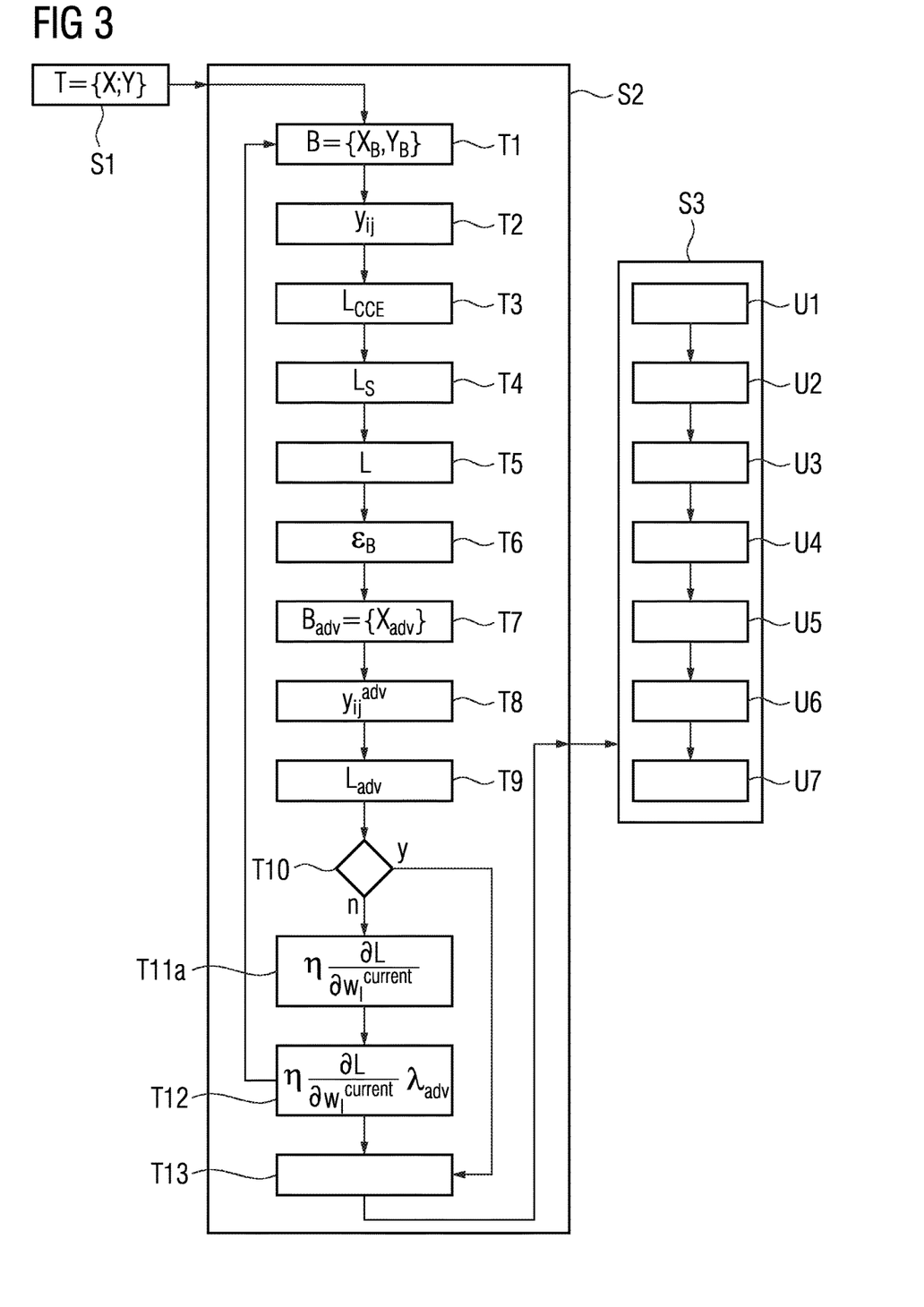
FIG. 3 shows a schematic flow chart of the method of training a NN according to a third aspect.

In FIG. 3 the method of training a NN according to the third aspect is schematically depicted. The method according to the third aspect and as depicted in FIG. 3 is similar to the methods according to the first and second aspects and as depicted in FIGS. 1 and 2. Therefore, only differences between the three will be mentioned in the following. The step of training S2 the NN of the method of FIG. 3 comprises the training steps T1 to T3, T10 and T13 of the step of training S2 the NN of the methods of FIGS. 1 and 2. Further, the step of training S2 the NN of the method of FIG. 3 comprises the training steps T4 and T5 of the step of training S2 the NN of the method of FIG. 1. Also the training step of updating T11a weights of the step of training S2 the NN of the method of FIG. 1 is comprised by the step of training S2 the NN of the method of FIG. 3 as the training step first time updating T11a weights. Additionally, the step of training S2 the NN of the method of FIG. 3 comprises the training steps T6 to T9 and second time updating T12 of the step of training S2 the NN of the method of FIG. 2. Consequently, the method of FIG. 3 combines in its step of training S2 the training steps of the steps of training S2 of the methods of FIGS. 1 and 2.

The computer program according to the fourth aspect may comprise instructions which, when the program is executed by a computer, cause the computer to carry out the steps S1 to S3 including the respective training steps T1 to T3 and sub-steps U1 to U7 of the method according to any of the first, second and third aspect and as depicted in FIGS. 1 to 3.

Figure 4:
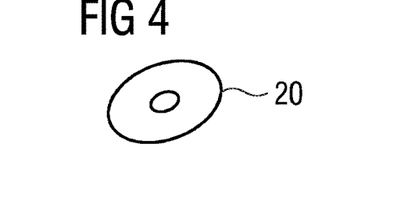
FIG. 4 shows a schematic view of the computer-readable medium according to a fifth aspect.

In FIG. 4 an embodiment of the computer-readable medium 20 according to the fifth aspect is schematically depicted.

Here, exemplarily a computer-readable storage disc 20 like a Compact Disc (CD), Digital Video Disc (DVD), High Definition DVD (HD DVD) or Blu-ray Disc (BD) has stored thereon the computer program according to the fourth aspect and as schematically shown in FIGS. 1 to 3. However, the computer-readable medium may also be a data storage like a magnetic storage/memory (e.g. magnetic-core memory, magnetic tape, magnetic card, magnet strip, magnet bubble storage, drum storage, hard disc drive, floppy disc or removable storage), an optical storage/memory (e.g. holographic memory, optical tape, Tesa tape, Laserdisc, Phasewriter (Phasewriter Dual, PD) or Ultra Density Optical (UDO)), a magneto-optical storage/memory (e.g. MiniDisc or Magneto-Optical Disk (MO-Disk)), a volatile semiconductor/solid state memory (e.g. Random Access Memory (RAM), Dynamic RAM (DRAM) or Static RAM (SRAM)), a non-volatile semiconductor/solid state memory (e.g. Read Only Memory (ROM), Programmable ROM (PROM), Erasable PROM (EPROM), Electrically EPROM (EEPROM), Flash-EEPROM (e.g. USB-Stick), Ferroelectric RAM (FRAM), Magnetoresistive RAM (MRAM) or Phase-change RAM).

Figure 5:
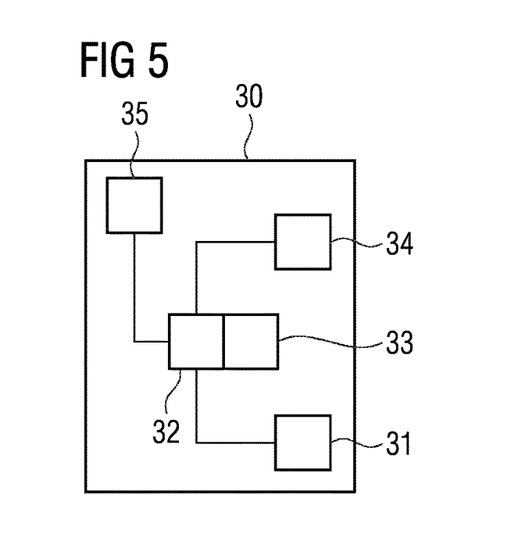
FIG. 5 shows a schematic view of the data processing system according to a sixth aspect.

In FIG. 5 an embodiment of the data processing system 30 according to the sixth aspect is schematically depicted.

The data processing system 30 may be a personal computer (PC), a laptop, a tablet, a server, a distributed system (e.g. cloud system) and the like. The data processing system 30 comprises a central processing unit (CPU) 31, a memory having a random access memory (RAM) 32 and a non-volatile memory (MEM, e.g. hard disk) 33, a human interface device (HID, e.g. keyboard, mouse, touchscreen etc.) 34 and an output device (MON, e.g. monitor, printer, speaker, etc.) 35. The CPU 31, RAM 32, HID 34 and MON 35 are communicatively connected via a data bus. The RAM 32 and MEM 33 are communicatively connected via another data bus. The computer program according to the fourth aspect and schematically depicted in FIGS. 1 to 3 can be loaded into the RAM 32 from the MEM 33 or another computer-readable medium 20. According to the computer program the CPU 31 executes the steps S1 to S3 including the respective training steps T1 to T3 and sub-steps U1 to U7 of the computer-implemented method according to any of the first, second and third aspect and as schematically depicted in FIGS. 1 to 3. The execution can be initiated and controlled by a user via the HID 34. The status and/or result of the executed computer program may be indicated to the user by the MON 35. The result of the executed computer program may be permanently stored on the non-volatile MEM 33 or another computer-readable medium.

In particular, the CPU 31 and RAM 32 for executing the computer program may comprise several CPUs 31 and several RAMs 32 for example in a computation cluster or a cloud system. The HID 34 and MON 35 for controlling execution of the computer program may be comprised by a different data processing system like a terminal communicatively connected to the data processing system 30 (e.g. cloud system).

Figure 6:
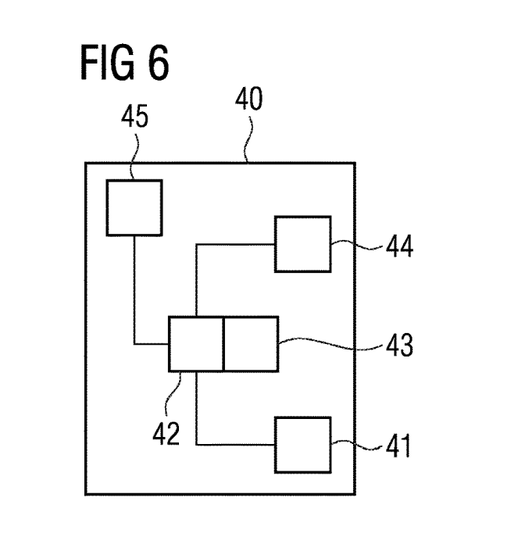
FIG. 6 shows a schematic view of the data processing system according to a seventh aspect.

In FIG. 6 an embodiment of the data processing system 40 according to the seventh aspect is schematically depicted.

The data processing system 40 may be a personal computer (PC), a laptop, a tablet, a server, a distributed system (e.g. cloud system) and the like. The data processing system 40 comprises a central processing unit (CPU) 41, a memory having a random access memory (RAM) 42 and a non-volatile memory (MEM, e.g. hard disk) 43, a human interface device (HID, e.g. keyboard, mouse, touchscreen etc.) 44 and an output device (MON, e.g. monitor, printer, speaker, etc.) 45. The CPU 41, RAM 42, HID 44 and MON 45 are communicatively connected via a data bus. The RAM 42 and MEM 43 are communicatively connected via another data bus. A trained NN that was trained with any of the methods according to the first, second and third aspect and as schematically depicted in FIGS. 1 to 3 can be loaded into the RAM 32 from the MEM 33 or another computer-readable medium 20. Accordingly, the trained NN is implemented on the data processing system 40 and the CPU 41 can execute predictions based on provided input data and the trained weights of the trained NN. The execution can be initiated and controlled by a user via the HID 44. The status and/or result of the executed prediction by the trained NN may be indicated to the user by the MON 45. The result may be permanently stored on the non-volatile MEM 43 or another computer-readable medium.

In particular, the CPU 41 and RAM 42 for implementing the trained NN may comprise several CPUs 41 and several RAMs 42 for example in a computation cluster or a cloud system. The HID 44 and MON 45 for controlling execution of the prediction by the NN may be comprised by a different data processing system like a terminal communicatively connected to the data processing system 40 (e.g. cloud system).

The first embodiment refers to the web service details of the proposed method. A transformation method for a trained AI model is described as part of a web service, which is accessible via a webpage. Just for example, the trained AI model might be generated based on a trained NN that was trained with any of the methods according to the aspects described above. The method is illustrated with FIG. 7, which is described in more detail in the following.

Figure 7:
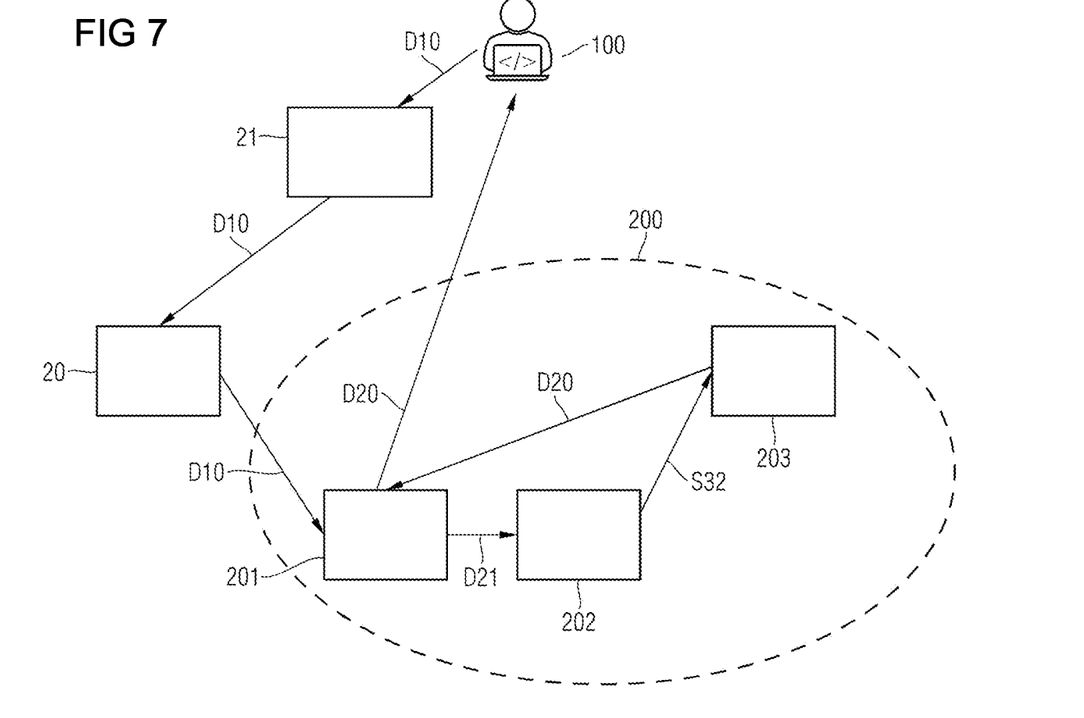
FIG. 7 shows a schematic representation of a system according to a first embodiment.

A user 100 for example accesses a webpage. The front end 20 of the webpage is for example realized via a web app, e.g. Elastic Beanstalk, which fetches an AWS EC2 instantiation. The web app askes the user 100 to upload a trained neural network, for example with weights exported in a pre-specified format, e.g. hdf5. In addition, it askes to provide a representative validation data set. These user data D10 is provided by the user 100 via the user interface and front end 20, which forwards it to a cloud platform 200.

According to the first embodiment, there is an additional authentication step realized with an authentication infrastructure 21, so that the user 100 is reliably identified and authenticated. For example, an e-mail address with password is used to register before the user 100 can upload the data. The user data D10 is therefore enhanced with user authentication information.

Within the cloud platform 200, a memory 201, e.g. a memory provided by AWS S3, a web-based Cloud Storage Service, saves the uploaded user data D10. An event within the AWS S3, which indicates the request for a transformation, is sent as notification D21 to a so-called Lambda function as trigger 202 for the actual transformation method.

The Lambda function is configured so that it calls suitable transformation methods, which are arranged in containers and called depending on the user data D10. For example, the user data D10 also comprises an information about which transformation method is desired, e.g. a post-processing or a re-training, or about requirements in terms of delivery time etc.

The trigger 202, in this embodiment the Lambda function, starts for example a data processing-Engine for containers, e.g. AWS Fargate, with a trigger call S32 and provides user data location. The AI model transformation then is performed in the backend 203, for example with a container-orchestration service like AWS ECS, where the Fargate container is executed.

As a result of this transformation, the trustworthy AI model is generated with the method explained in detail in the various embodiments above.

The transformation of the AI model as web service is enabled due to the characteristics of the transformation method, in particular the dependence on the generated generic samples, where only a validation data set is necessary as input, and moreover the usage of a calibration optimization, which does not affect the architecture or structure of the AI model, so that a deployment of the trustworthy AI model on user side is guaranteed.

The trustworthy AI model as well as corresponding process protocols are saved as transformation result D20 in the memory 201 and finally provided to the user 100. This happens for example via an AWS S3 event that sends the transformation result D20 directly to the e-mail address of the authenticated user 100, which has been saved in the memory 201.

Figure 8:
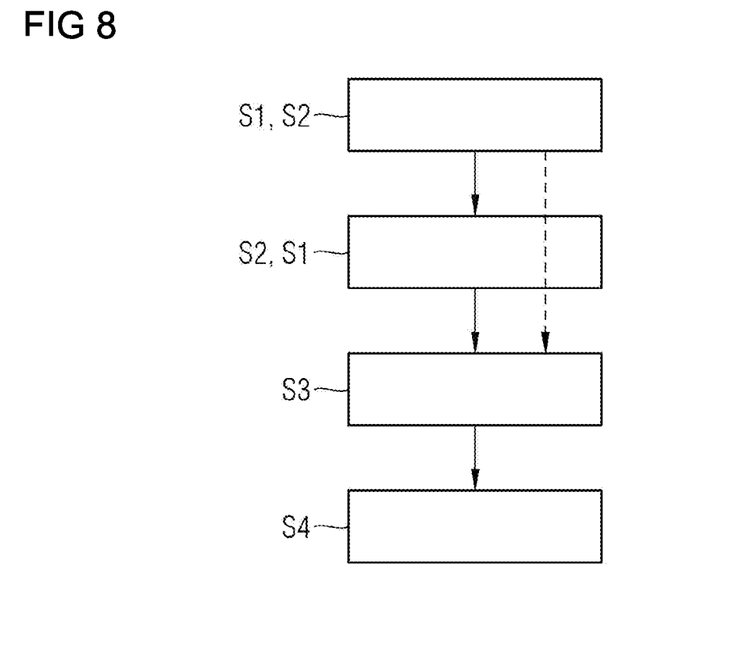
FIG. 8 shows a schematic flow chart diagram of a method corresponding to a second embodiment.

FIG. 8 shows a schematic flow chart diagram of a method, with the steps of providing S1 the trained artificial intelligence model via a user interface of a webservice platform, providing S2 a validation data set, which is based on training data of the trained artificial intelligence model,
generating S3 generic samples by a computing component of the webservice platform based on the validation data set, transforming S4 the trained artificial intelligence model by optimizing a calibration based on the generic samples.

The steps S1 and S2 of providing the trained artificial intelligence model and the validation data set might be performed decoupled of each other and in a flexible order, as indicated by the exchangeable reference signs in FIG. 8. In other embodiments, they can be combined and performed within one method step or simultaneously, as indicated by the dotted arrow.

The step of transforming the trained artificial intelligence model is explained in more detail.

A cross entropy loss term is defined as $$\mathcal{L}_j = \sum_{j=1}^{K} -y_{ij}\log(p_{ij})$$

and a uniform loss term as $$\mathcal{L}_{uniform_i} = \lambda_t \sum_{j=1}^{K} -\frac{1}{K}\log(p_{ij}(1-y_{ij}) + y_{ij})$$

with p being the prediction, y a label, $\lambda_t$ an annealing coefficient, t an index of a training step, i an index of a sample, j an index of a class and K the number of classes. This term encourages the model towards a uniformly distributed softmax output in case of uncertainty.

A calibration loss term is defined as $$\mathcal{L}_{ECE_i} = \|ECC_{gen_i}\|_2^2$$

$$ECE = \sum_{m=1}^{M} \frac{|B_m|}{n} |acc(B_m) - conf(B_m)|$$

with $ECC_{gen}$ being the ECE on the generic samples, with $B_m$ being the set of indices of samples whose prediction confidence falls into its associated interval $I_m$. $conf(B_m)$ and $acc(B_m)$ are the average confidence and accuracy associated to $B_m$ respectively, n the number of samples in the dataset, M a number of bins and m an index of bins. With this calibration loss term, which could be seen as generic calibration loss term, the technical robustness of the AI model for input around an epsilon-neighborhood of the training samples is increased.

These three loss terms are combined for retraining the AI model. As a result of the re-training, the trained AI model has been transformed into a trustworthy AI model, which yields confidence scores matching the accuracy for samples representing a domain shift, in particular gradually shifting away from samples of the validation data set.

Figure 9:
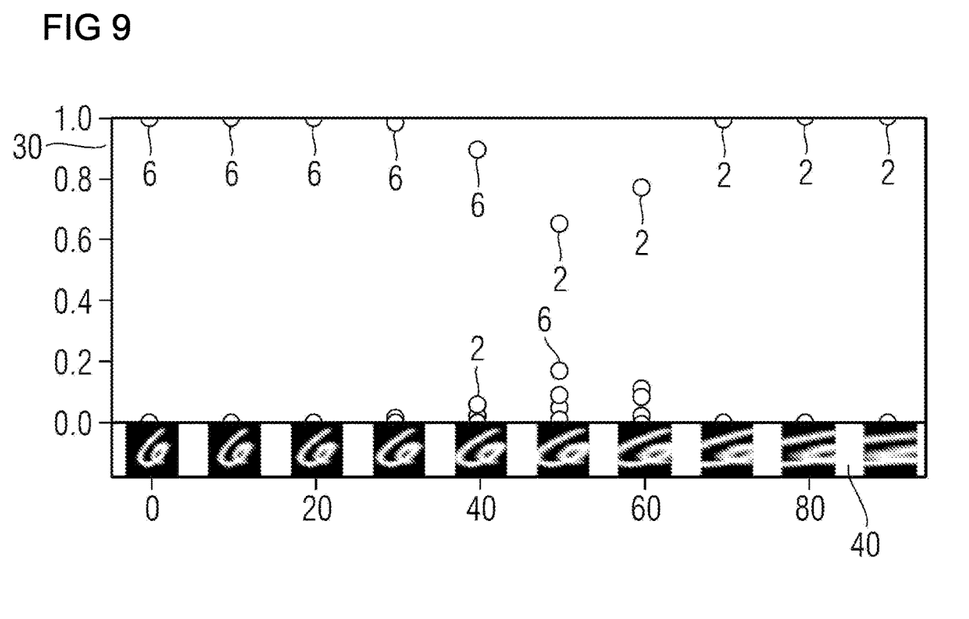
FIG. 9 shows a schematic diagram of an output of an AI model according to the state of the art.

FIG. 9 illustrates a result of an AI model according to the state of the art, showing a schematic diagram of an output of a classifier. On the vertical axis 30 of the diagram, the confidence scores are shown, on the horizontal axis 40, the discrete input data is shown. From left to right, the quality of the input data, here in form of a handwritten figure "6", decreased due to a distortion in one direction. Those kinds of distortion reflect effects on data input in real life scenarios, which impede accurate prediction of the classifier.

The classifier is trained to assign one of 10 classes to the input data, corresponding to FIGS. 0-9.

As one can see, starting at about a range of perturbation of 50, which represents a flexible and arbitrary scale to group distortions and might be a value of epsilon, which has been introduced in the description above, the classifier starts to predict a wrong classification result, "2" in this case, but with a high confidence score over 60%, even increasing with increasing epsilon up to almost 100%. This illustrates an over-confident classifier when data with domain shift is to be classified.

Figure 10:
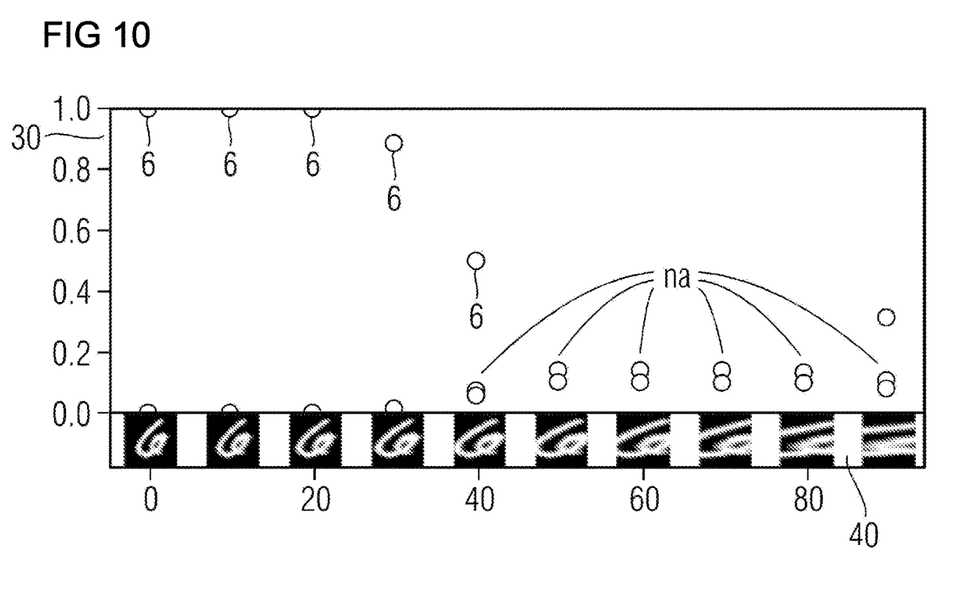
FIG. 10 shows a schematic diagram of an output of a trustworthy AI model according to a third embodiment.

According to the third embodiment, which is illustrated in FIG. 10, the same classifier is used, but the underlying AI classification model has been transformed into a trustworthy AI model with the following method.

A set of samples are generated which cover the entire spectrum from in-domain samples to truly out-of-domain samples in a continuous and representative manner. According to this, the fast gradient sign method (FGSM) is used on the basis of the validation data set with sample pairs to generate perturbated samples, with varying perturbation strength. More specifically, for each sample pair in the validation data set, the derivative of the loss is determined with respect to each input dimension and the sign of this gradient is recorded. If the gradient cannot be determined analytically (e.g. for decision trees), it can be resorted to a 0th-order approximation and the gradient can be determined using finite differences. Then, noise $epsilon$ is added to each input dimension in the direction of its gradient. For each sample pair, a noise level can be selected at random, such that the generic data set comprises representative samples from the entire spectrum of domain drift, as shown in the pseudo code of algorithm 1 and explanation.

```
\begin{algorithm}[H]
    \caption{PORTAL with trained neural network $f(x)$, a set of perturbation levels
$\mathcal{E}=\{  0.001,0.002,0.004,0.008,0.016,0.032,0.064,0.128,0.256,0.512\}$ ,
complexity parameter $\zeta=1$, validation set $(X, Y)$, and empty perturbed validation
set $(X_\mathcal{E},Y_\mathcal{E}, Z_\mathcal{E}, Z`r_\mathcal{E})$.
    }\label{alg1}
    \begin{algorithmic}[1]
    \For{(x, y) in (X,Y)}
```

```
    \For{$\epsilon\; \mathrm{in}\; \mathcal{E}$}
        \State Generate generic sample $x_\epsilon$ using $\epsilon_\zeta=\epsilon/\zeta$
        \State Use neural network $f(x_\epsilon)$ to compute unnormalized logits
$\bm{z_\epsilon}$ and logit range $z_\epsilon^r$
        \State Add $(x_\epsilon, y, \bm{z_\epsilon}, z_\epsilon^r)$ to
$(X_\mathcal{E},Y_\mathcal{E}, Z_\mathcal{E}, Z^r_\mathcal{E})$
    \EndFor
\EndFor
    \State Initialize $\bm{\theta}$
    \State Optimize $\bm{\theta}$ using Nelder-Mead optimizer for log-likelihood of
perturbed validation set $\mathcal{L}(\bm{\theta}) = - \sum_{i=1}^{N_\mathcal{E}} y_i
\log \hat{Q}_i(\bm{ \theta}) = - \sum_{i=1}^{N_\mathcal{E}} y_i \log
\sigma_{SM}(\mathbf{z}_i/T(z^r_i;\bm{\theta}))$
    \end{algorithmic}
\end{algorithm}
```

Algorithm 1 Generation of generic data set $V_g$ based on validation V, consisting of a collection of labelled samples $\{(x,y)\}$, with x being model inputs an y model outputs. N denotes the number of samples in V, $\varepsilon=\{0,0.05,0.1,0.15,0.2, 0.025,0.3,0.35,0.4,0.45\}$ the set of perturbation levels.

Require: Validation set V and empty generic data set $V_g$
1: for i in 1:N do
2: Read sample pair $(x_i, y_i)$ from V
3: Randomly sample $\epsilon_i$ from $\varepsilon$
4: Generate generic sample pair $(x_g, y)$ using the FGSM method based on $\epsilon_i$
5: Add $(x_g, y)$ to $V_g$
6: end for $x_g$ denotes a generic input generated from x using the FGSM method.

According to an alternative embodiment, the formulation of Algorithm 1 differs in that not only one generic sample is generated per sample pair; but instead FGSM is applied for all available epsilons. Thereby the size of the generic data set can be significantly increased by the size of the set of epsilons. In other words, different perturbation strategies can be used e.g. based on image perturbation. An advantage is that the method according to embodiments of the invention can be applied on black box models where it is not possible to compute the gradient.

Next, a strictly monotonic parameterized function is used to transform the unnormalized logits of the classifier. For example, Platt scaling, temperature scaling, other parameterizations of a monotonic function, or non-parametric alternatives can be used. In an embodiment according to the following equation a novel parameterization is used, which adds additional flexibility to known functions by introducing range-adaptive temperature scaling. While in classical temperature scaling a single temperature is used to transform logits across the entire spectrum of outputs, a range-specific temperature is used for different value ranges.

The following is a formula of an embodiment:

$$T(z^r; \theta) = \exp\_id\left(\frac{\theta_1}{(z^r + \theta_2)^{\theta_3}} + \theta_0\right) \quad (5)$$

with $\theta=[\theta_0, \ldots \theta_3]$ parameterizing the temperature $T(z^r; \theta)$ and $z_r=\max(z)-\min(z)$ being the range of an unnormalized logits tuple z. $\theta_0$ can be interpreted as an asymptotic dependency on $z^r$. The following function an be used exp_id: $x \to \{x+1, x>0; \exp(x), \text{else}\}$ to ensure a positive output. This parameterized temperature is then used to obtain calibrated confidence scores $\hat{Q}_i$ for sample i based on unnormalized logits:

$$\hat{Q}_i = \max_c \sigma_{SM}(z_i/T(z_i^r; \theta))^{(c)} \quad (6)$$

$$\int c, T : \mathbb{R} \to \mathbb{R}$$

$$\int c, T : x \to$$

$$\begin{cases} \frac{x}{|T_1|} & \text{if } x < C_1 \\ \frac{x - C_h - 1}{|Th|} + \sum_{l=1}^{h-1} \frac{C_l - C_{l-1}}{|Tl|} & \text{if } C_{h-1} \le x < C_h, \ h = 2, \ldots, H \end{cases}$$

with $H := \dim(T)$ $c_0 := 0$, $c_H := \infty$

Sigma_SM denotes the softmax function. The parameters of the function (theta) are then determined by optimizing a calibration metric based on the generic data set. Calibration metrics can be the log likelihood, the Brier score or the expected calibration error, see also Algorithm 2.

Algorithm 2 Fit parameterized post-processing model $u=\int(z,T)$, where $\int$ is a strictly monotonic function parameterized by parameters T and maps the unnormalized logits $z=C(x)$ of a classifier C to transformed (still unnormalized) logits u. Let g denote a calibration metric that is used to compute a scalar calibration measure w based on a set of logits along with ground truth labels.

Require: Generic set $V_g$ (from algorithm 1), function $\int$ with initial parameters T, calibration metric g.
1: repeat
2: Read sample pairs $\{(x_g,y)\}$ from $V_g$. Let Y be the set of all labels.
3: Compute post-processed logits $u=\int(z,T)$ for all $z=C(x_{adv})$, comprising set U.
4: Perform optimization step and update T to optimize $g(U,Y)$
5: until Optimisation converged
6: return Optimized T In an alternative embodiment of a blackbox classifier where logits are not available, Algorithm 2 can be adapted such that unnormalized logits are generated by computing $z=\log(C(x))$. Optimizers can advantageously be selected according to the form of the metric (e.g. Nelder Mead for piecewise temperature scaling) in a flexible manner.

After the trained AI classification model has been transformed with the method described, the same input data as used in connection with the state of the art model from FIG. 9 is now used to be classified by the trustworthy AI classification model. As one can see from FIG. 10, up to a perturbation level of 20, the right class "6" is predicted with the same high confidence as predicted with the prior art method. The confidence level decreases slightly from almost 100% to about 80% for a perturbation level of 30. For 40, there is already a confidence level for the predicted class of only around 50%, so that there is a clear indication, that the prediction is subject to uncertainty. Up from epsilon 50, the trustworthy AI classifier gives a prediction rate of about 10% for essentially all classes na. This translates to a result "no classification possible with sufficient certainty", so that all of the ten classes might be the correct prediction, leading to a confidence score of ⅟10 or 10%.

The transformed trustworthy AI model can in an advantageous manner be used be a non-expert user in an application for AI-based classifying also in safety-critical applications, where a timely recognition of decreasing accuracy for prediction also for input data under domain drift is key and over-confident estimates have to be avoided.

Although specific embodiments have been illustrated and described herein, it will be appreciated by those of ordinary skill in the art that a variety of alternate and/or equivalent implementations exist. It should be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope. Generally, this application is intended to cover any adaptations or variations of the specific embodiments discussed herein.

In the foregoing detailed description, various features are grouped together in one or more examples for the purpose of streamlining the disclosure. It is understood that the above description is intended to be illustrative, and not restrictive. It is intended to cover all alternatives, modifications and equivalents as may be included within the scope of embodiments of the invention. Many other examples will be apparent to one skilled in the art upon reviewing the above specification.

Specific nomenclature used in the foregoing specification is used to provide a thorough understanding of embodiments of the invention. However, it will be apparent to one skilled in the art in light of the specification provided herein that the specific details are not required in order to practice embodiments of the invention. Thus, the foregoing descriptions of specific embodiments of the present invention are presented for purposes of illustration and description. They are not intended to be exhaustive or to limit embodiments of the invention to the precise forms disclosed; obviously many modifications and variations are possible in view of the above teachings. The embodiments were chosen and described in order to best explain the principles of embodiments of the invention and its practical applications, to thereby enable others skilled in the art to best utilize embodiments of the invention and various embodiments with various modifications as are suited to the particular use contemplated. Throughout the specification, the terms "including" and "in which" are used as the plain-English equivalents of the respective terms "comprising" and "wherein," respectively. Moreover, the terms "first," "second," and "third," etc., are used merely as labels, and are not intended to impose numerical requirements on or to establish a certain ranking of importance of their objects. In the context of the present description the conjunction "or" is to be understood as including ("and/or") and not exclusive ("either . . . or").

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

The invention claimed is:

1. A computer-implemented method for transforming a trained artificial intelligence model into a trustworthy artificial intelligence model, comprising:
providing the trained artificial intelligence model via a user interface of a webservice platform, providing a validation data set, which is based on training data of the trained artificial intelligence model,
generating generic samples by a computing component of the webservice platform based on the validation data set, wherein for generating the generic samples the validation data set is modified by a domain-drift, and
transforming the trained artificial intelligence model by optimizing a calibration based on the generic samples, wherein by optimizing the calibration, an uncertainty-awareness is represented in a confidence-level for any of the generic samples.

2. The method according to claim 1, wherein for generating the generic samples the validation data set is modified according to perturbation strengths.

3. The method according to claim 1, wherein transforming comprises performing a re-training of the AI-model with applying an entropy-based loss term which encourages uncertainty-awareness.

4. The method according to claim 3, wherein transforming further comprises applying a calibration loss term.

5. The method according to claim 3, comprising the steps of:
generating current outputs of the AI model for the validation data set by forward propagating validation input data of the validation data set in the AI model;
computing a categorical cross-entropy loss $L_{CCE}$ for the validation data set based on the current outputs and corresponding ground truth data of the validation data set;
computing a predictive entropy loss $L_S$ by removing non-misleading evidence from the current outputs and distributing the remaining current outputs over a predetermined number C of classes;
computing a combined loss L by adding to the categorical cross-entropy loss $L_{CCE}$ the predictive entropy loss $L_S$ weighted with a predetermined first loss factor $\lambda_S$, where $0<=\lambda_S<=1$;
checking whether the re-training converged to a predefined lower limit for a convergence rate;
updating weights of the AI model based on the combined loss L and a predetermined training rate $\eta$, where $0<\eta<=1$, in case the re-training did not converge; and
stopping the re-training of the AI model in case the re-training converged.

6. The method according to claim 5, further comprising the steps of:

generating perturbed outputs of the AI model for the generic samples by forward propagating the generic input data $X_{adv}$ of the generic samples in the AI model;

computing a calibration loss $L_{adv}$ as the Euclidian norm, $L_2$ norm, of an expected calibration error ECE, which takes a weighted average over the perturbed outputs grouped in a predefined number M of equally spaced bins each having an associated average confidence and accuracy, where M>1;

checking whether the re-training converged to a predefined lower limit for a convergence rate;

first time updating weights of the AI model based on the combined loss L and a predetermined training rate $\eta$, where 0<$\eta$<=1, in case the training did not converge;

second time updating the weights of the AI model based on the calibration loss $L_{adv}$ weighted with a predetermined second loss factor $\lambda_{adv}$, where 0<=$\lambda_{adv}$<=1, and the predetermined training rate $\eta$, in case the training did not converge; and stopping the training of the AI model in case the training converged.

7. The method according to claim 3, wherein the artificial intelligence model is a neural network.

8. The method according to claim 1, wherein transforming comprises post-processing an output of the AI model.

9. The method according to claim 8, wherein during the step of post-processing, parameters of a monotonic function used to transform unnormalized logits are determined by optimizing a calibration metric based on the generic samples.

10. The method according to claim 8, wherein the artificial intelligence model is a classifier.

11. The method according to claim 1, wherein the validation data set is a sub-set of the training data of the trained artificial intelligence model.

12. The method according to claim 1, wherein the validation data set is generated by modifying the training data of the trained artificial intelligence model.

13. The method according to claim 1, wherein the transformed artificial intelligence model is provided via the user interface of the webservice platform.

14. A computer program product, comprising a computer readable hardware storage device having computer readable program code stored therein, said program code executable by a processor of a computer system to implement the method according to claim 1.

15. A system for transforming a trained artificial intelligence model into a trustworthy artificial intelligence model, comprising:
a user interface component to enable provision of the trained artificial intelligence model,
a memory storing the trained artificial intelligence model and user assignment information, and
a computing component for generating generic samples based on a validation data set, wherein the validation data set is determined based on training data of the trained artificial intelligence model, wherein for generating the generic samples the validation data set is modified by a domain-drift, and for transforming the trained artificial intelligence model by optimizing a calibration based on the generic samples, wherein by optimizing the calibration, an uncertainty-awareness is represented in a confidence-level for any of the generic samples.

16. The system according to claim 15, wherein the user interface component is accessible via a webservice.

17. The system according to claim 15, wherein the memory and the computing component are implemented on a cloud platform.

18. A computer-implemented method for transforming a trained artificial intelligence model into a trustworthy artificial intelligence model, comprising:
providing the trained artificial intelligence model via a user interface of a webservice platform,
providing a validation data set, which is based on training data of the trained artificial intelligence model,
generating generic samples by a computing component of the webservice platform based on the validation data set,
transforming the trained artificial intelligence model by optimizing a calibration based on the generic samples, wherein transforming comprises performing a re-training of the AI-model with applying an entropy-based loss term which encourages uncertainty-awareness,
generating current outputs of the AI model for the validation data set by forward propagating validation input data of the validation data set in the AI model;
computing a categorical cross-entropy loss $L_{CCE}$ for the validation data set based on the current outputs and corresponding ground truth data of the validation data set;
computing a predictive entropy loss $L_S$ by removing non-misleading evidence from the current outputs and distributing the remaining current outputs over a predetermined number C of classes;
computing a combined loss L by adding to the categorical cross-entropy loss $L_{CCE}$ the predictive entropy loss $L_S$ weighted with a predetermined first loss factor $\lambda_S$, where 0<=$\lambda_S$<=1;
checking whether the re-training converged to a predefined lower limit for a convergence rate;
updating weights of the AI model based on the combined loss L and a predetermined training rate $\eta$, where 0<$\eta$<=1, in case the re-training did not converge; and
stopping the re-training of the AI model in case the re-training converged.

19. The method according to claim 18, further comprising the steps of:
generating perturbed outputs of the AI model for the generic samples by forward propagating the generic input data $X_{adv}$ of the generic samples in the AI model;
computing a calibration loss $L_{adv}$ as the Euclidian norm, $L_2$ norm, of an expected calibration error ECE, which takes a weighted average over the perturbed outputs grouped in a predefined number M of equally spaced bins each having an associated average confidence and accuracy, where M>1;
checking whether the re-training converged to a predefined lower limit for a convergence rate;
first time updating weights of the AI model based on the combined loss L and a predetermined training rate $\eta$, where 0<$\eta$<=1, in case the training did not converge;
second time updating the weights of the AI model based on the calibration loss $L_{adv}$ weighted with a predetermined second loss factor $\lambda_{adv}$, where 0<=$\lambda_{adv}$<=1, and the predetermined training rate $\eta$, in case the training did not converge; and
stopping the training of the AI model in case the training converged.

\* \* \* \* \*